United States Patent
Libbus et al.

(10) Patent No.: US 7,672,728 B2
(45) Date of Patent: Mar. 2, 2010

(54) NEURAL STIMULATOR TO TREAT SLEEP DISORDERED BREATHING

(75) Inventors: Imad Libbus, St. Paul, MN (US); Anthony Caparso, St. Louis Park, MN (US); M. Jason Brooke, Minneapolis, MN (US); Jonathan Kwok, Shoreview, MN (US); Kent Lee, Shoreview, MN (US); Yachuan Pu, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1031 days.

(21) Appl. No.: 11/320,500

(22) Filed: Dec. 28, 2005

(65) Prior Publication Data

US 2007/0150006 A1    Jun. 28, 2007

(51) Int. Cl.
*A61N 1/00*    (2006.01)
(52) U.S. Cl. ........................................ 607/42
(58) Field of Classification Search .................... 607/42, 607/62, 23, 24, 2, 9–18, 26, 116; 600/544, 600/378
See application file for complete search history.

(56) References Cited

U.S. PATENT DOCUMENTS

| | | | |
|---|---|---|---|
| 5,174,287 A | 12/1992 | Kallok et al. | |
| 5,190,053 A | 3/1993 | Meer | |
| 5,314,454 A * | 5/1994 | Jaeger et al. | 607/62 |
| 5,335,657 A * | 8/1994 | Terry et al. | 607/45 |
| 5,591,216 A | 1/1997 | Testerman et al. | |
| 6,240,316 B1 | 5/2001 | Richmond et al. | |
| 6,269,269 B1 | 7/2001 | Ottenhoff et al. | |
| 6,456,866 B1 | 9/2002 | Tyler et al. | |
| 6,770,022 B2 | 8/2004 | Mechlenburg et al. | |
| 7,025,730 B2 * | 4/2006 | Cho et al. | 600/529 |
| 7,155,278 B2 * | 12/2006 | King et al. | 607/2 |
| 7,194,313 B2 | 3/2007 | Libbus | |
| 7,277,761 B2 | 10/2007 | Shelchuk | |
| 2004/0193068 A1 * | 9/2004 | Burton et al. | 600/544 |
| 2004/0210261 A1 | 10/2004 | King et al. | |

(Continued)

OTHER PUBLICATIONS

Bradley, T.D., et al., "Sleep Apnea and Heart Failure, Part I: Obstructive Sleep Apnea", *Special Review, Circulation*, vol. 107, (2003), 1671-1678.

(Continued)

*Primary Examiner*—George Manuel
*Assistant Examiner*—Robert N Wieland
(74) *Attorney, Agent, or Firm*—Schwegman, Lundberg & Woessner, P.A.

(57) ABSTRACT

Various aspects relate to an implantable device. Various device embodiments include at least one sensor for use in detecting sleep disordered breathing, a pulse generator adapted to deliver a first electrical signal through at least one electrode to stimulate a neural target, and a controller adapted to communicate with the at least one sensor and with the pulse generator. The controller is adapted to detect sleep disordered breathing using the at least one sensor and provide a therapy for sleep disordered breathing in response to a detected apneic event. The therapy for sleep disordered breathing is adapted to deliver the first electrical signal through the at least one electrode to induce a cough reflex to terminate the apneic event. Various embodiments stimulate a superior laryngeal nerve, various embodiments stimulate a recurrent laryngeal nerve, and various embodiments stimulate a vagus nerve. Other aspects and embodiments are provided herein.

33 Claims, 11 Drawing Sheets

U.S. PATENT DOCUMENTS

| | | |
|---|---|---|
| 2005/0143785 A1 | 6/2005 | Libbus |
| 2005/0288728 A1 | 12/2005 | Libbus et al. |
| 2005/0288729 A1 | 12/2005 | Libbus et al. |
| 2006/0293604 A1 | 12/2006 | Carlson et al. |
| 2008/0161894 A1* | 7/2008 | Ben-David et al. .......... 607/116 |

OTHER PUBLICATIONS

Bradley, T. D., et al., "Sleep Apnea and Heart Failure, Part II: Central Sleep Apnea", *Special Review, Circulation*, vol. 107, (2003),1822-1826.

Garrigue, S, et al., "Benefit of Atrial Pacing in Sleep Apnea Syndrome", *The New England Journal of Medicinem* 346(6), (2002), 404-412.

Leventhal, D K., et al., "Subfascicle Stimulation Selectivity with the Flat Interface Nerve Electrode", *Annals of Biomedical Engineering*, 31(6), (2003), 643-652.

Sinha, A.-M., et al., "Cardiac Resynchronization Therapy Improves Central Sleep Apnea and Cheyne-Stokes Respiration in Patients with Chronic Heart Failure", *Journal of the American College of Cardiology*, 44(1), (2004), 68-71.

Walsh, J., et al., "Cough", [online]. Retrieved from the Internet: <URL: www.lumen.luc.edu/lumen>, (Jan. 1, 1996), 4 pgs.

Yoo, P., et al., "Effects of Selective Hypoglossal Nerve Stimulation on Canine Upper Airway Mechanics", *J Appl Physiol*, 99, (2005), 937-943.

* cited by examiner

NEURAL STIMULATOR TO TREAT SLEEP DISORDERED BREATHING

TECHNICAL FIELD

This application relates generally to medical devices and, more particularly, to devices to treat sleep disordered breathing.

BACKGROUND

Respiratory disorders during sleep include sleep apnea (cessation of breathing) and hypopnea (abnormally slow or shallow breathing). Sleep apneas are among the most common chronic disorders in adults, and can cause excessive day time sleepiness and can increases risks for cardiovascular diseases.

Studies have indicated that both sleep apnea and hypopnea have serious health consequences, including an association with cardiac arrhythmias and congestive heart failure (CHF). The majority of a normal sleep pattern is non-rapid eye movement (NREM) sleep and a minority of a normal sleep pattern is rapid eye movement (REM) sleep. NREM sleep is a state of cardiovascular relaxation, reflected in an increase in vagal activity and a decrease in metabolic rate, sympathetic nervous system activity, heart rate, cardiac output, and systemic vascular resistance. REM sleep involves intermittent surges in sympathetic discharge, heart rate, and blood pressure. Many patients with heart failure have obstructive sleep apnea and/or central sleep apnea, both of which disrupt the normal relaxing effects of sleep on the cardiovascular system, and can result in intermittent apnea-induced hypoxia, hypercapnia, surges in central sympathetic outflow and afterload, daytime hypertension, and loss of vagal heart rate regulation, which can stimulate myocyte necrosis and apopsis, myocardial ischemia, arrhythmias, adverse cardiac remodeling and accelerated disease progression in heart failure. Obstructive sleep apnea and heart failure both adversely impact sympathetic nervous activation and vagal withdrawal of the cardiovascular system in general, and both detrimentally alter loading conditions and hypoxia on the ventricle.

Efforts for treating sleep disordered breathing have included continuous positive airway pressure (CPAP), atrial overdrive pacing, and CRT pacing. Other proposed methods for treating sleep disordered breathing include the stimulation of motor nerves and direct stimulation of the muscles of the upper airway.

SUMMARY

Various aspects of the present subject matter relate to an implantable device. Various device embodiments include at least one sensor for use in detecting sleep disordered breathing, a pulse generator adapted to deliver a first electrical signal through at least one electrode to stimulate a neural target, and a controller adapted to communicate with the at least one sensor and with the pulse generator. The controller is adapted to detect sleep disordered breathing using the at least one sensor and provide a therapy for sleep disordered breathing in response to a detected apneic event. The therapy for sleep disordered breathing is adapted to deliver the first electrical signal through the at least one electrode to induce a cough reflex to terminate the apneic event. Various embodiments stimulate a superior laryngeal nerve, various embodiments stimulate a recurrent laryngeal nerve, and various embodiments stimulate a vagus nerve.

Various aspects of the present subject matter relate to a method. According to various method embodiments, a sleep disordered event is detected, and an autonomic neural target is stimulated to induce a cough to terminate the sleep disordered event in response to a detected sleep disordered event.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1A:
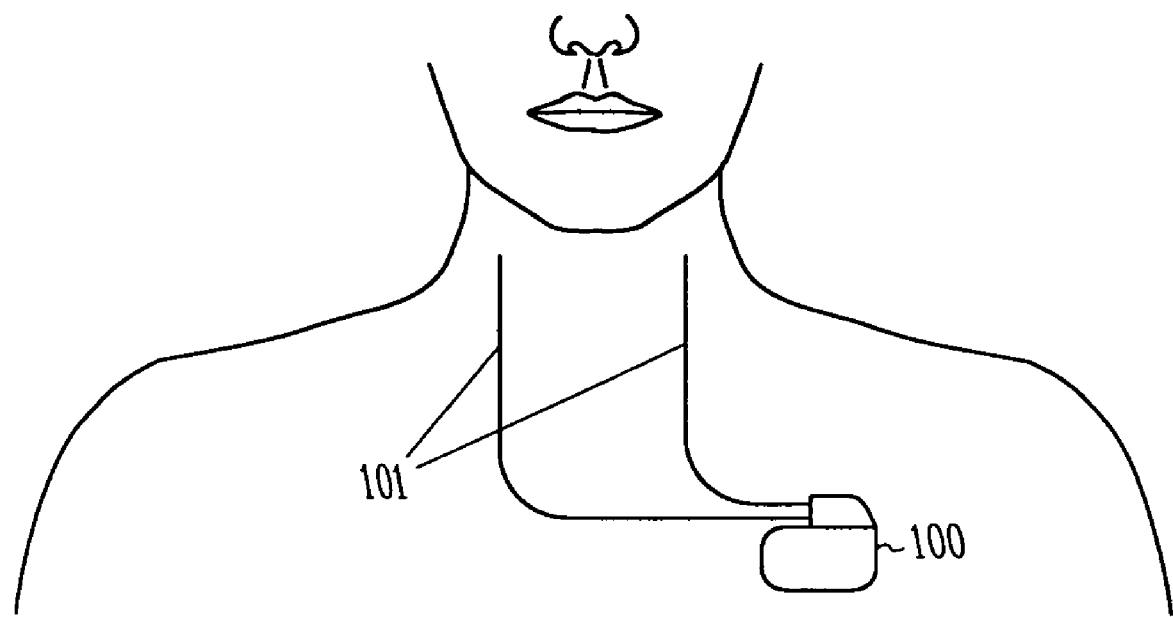
FIGS. 1A-1B illustrate some device embodiments that provide therapy for sleep disordered breathing.

The present subject matter treats sleep disordered breathing using autonomic nerve stimulation to treat sleep disordered breathing. Embodiments provide an implantable neural stimulator to treat obstructive sleep apnea using neural stimulation of autonomic neural targets. The device monitors physiological parameters (e.g. heart rate, minute ventilation, etc.) and detects the incidence of sleep apnea. When such an event is detected, a short burst of stimulation is applied to a selected neural target, inducing a mild cough and terminating the apneic event. Respiratory sensors provide feedback to verify the induction of the cough, and neural stimulation parameters will be adjusted to induce an appropriate cough level to terminate the apneic event without waking the patient.

The present subject matter is able to deliver therapy when a period of disordered breathing is detected during sleep. Other therapies, such as the continuous positive airway pressure (CPAP) device, provide therapy to the patient continuously during the night. CPAP therapy suffers from compliance problems that are not present with implantable therapies. Some embodiments function in cooperation with other sleep disordered breathing therapies. For example, if the primary therapy (such as CPAP) fails, a secondary therapy (such as neural stimulation, cardiac pacing, respiratory pacing, or a combination) may be delivered.

The present subject matter can be implemented as a stand alone implantable device for sleep apnea therapy. The device may also act in cooperation with other sleep disordered breathing therapies, such as CPAP or cardiac pacing. This neural stimulation therapy can be implemented as part of a cardiac rhythm management (CRM) device, or the neural stimulation therapy can be otherwise implemented with the CRM therapy, thus addressing the co-morbidity of sleep apnea and cardiac arrhythmias and heart failure. Thus, the present subject matter may also provide the ability to provide a cardiac rhythm management therapy such as cardiac pacing, atrial and/or ventricular defibrillation, and/or the ability to provide cardiac resynchronization therapy (CRT). This device could be implemented in a subcutaneous configuration (i.e. without intravascular leads), with or without additional CRM capabilities such as subcutaneous cardiac sensing and defibrillation.

Some IMD embodiments provide neural stimulation therapy to at least one autonomic neural target selected from the superior laryngeal nerve, the inferior (recurrent) laryngeal nerve, and the vagus nerve. Some embodiments directly stimulate the target nerve using a nerve cuff, for example; and some embodiments indirectly stimulate the neural target using transvascular stimulation using an electrode within a vessel proximate to the neural target. The neural stimulation to the neural target is adapted to induce a cough to open the airway and terminate the apneic event. The stimulation can be applied to produce a mild cough that does not awaken the patient with the sleep apnea. The coughing reflex is stimulated through afferent or efferent means. In the coughing reflex, thoracic and abdominal expiratory muscles contract, forcing air out of the chest and opening the upper airway. The cough reflex is characterized by a deep inspiration followed by glottic closure, diaphragmatic relaxation, and thoracic and abdominal expiratory muscle contraction. Cough receptors, afferent nerves, and efferent nerves can stimulate the cough reflex. Cough receptors include extrathoracic receptors found in the nose oropharynx, larynx and upper trachea, intrathoracic receptors that are rapidly adapting irritant receptors found in the epithelium of lower trachea and large central bronchi. Cough receptors can be found in other locations, such as the tympanic membrane, diaphragm and stomach. Examples of afferent nerves that can stimulate the cough reflex include the trigeminal, glossopharyngeal, superior laryngeal and vagus nerves. An observed effect of vagal nerve stimulation is increased coughing. Examples of efferent nerves that can stimulate the cough reflex include the recurrent laryngeal, vagus, corticospinal tract, and peripheral nerves.

Various IMD embodiments determine that the patient is asleep, and monitor one or more signals associated with sleep-disordered breathing. Examples of monitored signals include body movement, heart rate, QT interval, eye movement, respiration rate, transthoracic impedance, tidal volume, minute ventilation, body posture, electroencephalogram (EEG), electroneurogram (ENG), electrocardiogram (ECG), electrooculogram (EOG), electromyogram (EMG), muscle tone, body temperature, pulse oximetry, and time of day. Various device embodiments use any one or any combination of two or more of these signals to determine the incidence of sleep-disordered breathing. If disordered breathing is detected, neural stimulation is applied. The neural stimulation can be applied directly through a nerve cuff or indirectly through an intravascularly positioned electrode, for example. The neural stimulation electrode(s) are positioned in an appropriate location to stimulate the superior laryngeal nerve, inferior (recurrent) laryngeal nerve, and/or vagus nerve to induce a mild cough that opens the airway and terminates the apnea event. Coughing involves a sudden chest movement, and can be detected with a variety of sensors, such as acoustic sensors (e.g. accelerometer based), motion sensors (e.g. accelerometer based), thoracic pressure sensors, trans-thoracic impedance sensor, respiratory effort sensors, flow sensors, and diaphragm EMG. Induced coughing levels can be used to modulate neural stimulation parameters (amplitude, frequency, etc.) in a closed-loop fashion. The stimulation can be titrated in a manner as to not change the patient's sleep quality. The neural stimulator may also include the capability to trend and store physiological variables, with the goal of predicting and automating delivery of neural stimulation. Trending and prediction algorithms may be performed by the device itself, or by an external unit which communicates with the device such as in an advanced patient management (APM) system.

AUTONOMIC NERVE STIMULATION TO TREAT SLEEP DISORDERED BREATHING

Embodiments of the present subject matter stimulate predetermined autonomic neural targets to induce a cough reflex sufficient to terminate apneic events. These neural targets can be stimulated through direct stimulation such as by a nerve cuff or indirect stimulation such as by transvascular stimulation using intravascularly-placed electrodes. The following provides some information regarding the cough reflex, and autonomic neural targets.

Cough Reflex

The cough reflex begins with deep inspiration, followed by glottic closure, relaxation of the diaphragm, and contraction of the thoracic and abdominal expiratory muscles. Components of the cough reflex includes cough receptors, afferent nerves, a cough center, efferent nerves and effector muscles. The cough receptors include extrathoracic receptors located in the nose, oropharynx, larynx, and upper trachea; intrathoracic receptors that are rapidly adapting irritant receptors in the epithelium of the lower trachea and large central bronchi; and receptors in other locations such as the tympanic membrane, diaphragm and stomach. The afferent nerves associated with the cough reflex include the trigeminal nerve, the glossopharyngeal nerve, the superior laryngeal nerve and the vagus nerve. The efferent nerves associated with the cough reflex include the recurrent laryngeal nerves, the vagus nerve, the corticospinal tract and peripheral nerves.

Autonomic Neural Targets

Embodiments of the present subject matter stimulate autonomic neural targets with an appropriate electrical signal to induce a mild cough. The strength or intensity of the cough is related to the amplitude of the stimulation signal, and thus can be controlled by controlling the amplitude of the stimulation signal. Embodiments of the present subject matter stimulate the superior laryngeal nerve and/or the recurrent laryngeal nerve using neural stimulation applied to these branches or using neural stimulation applied to select fibres of the vagus nerve. The following provides some information regarding the vagus nerve, and its relationship to the superior and recurrently laryngeal nerves.

The vagus nerve is a mixed nerve containing both motor and sensory fibres, that traverses and supplies structures in the neck, thorax and abdomen. Upon exiting the skull, the vagus nerve (cranial nerve X) travels between the internal jugular vein and the internal carotid artery. The vagus nerve includes a brachial motor or special visceral efferent function, a visceral motor or general visceral efferent function; a visceral sensory or general visceral afferent function, a general sensory or general somatic afferent function, and a special sensory or special afferent function. Branches of the vagus nerve include the meningeal branches, the auricular branch, the pharyngeal branch, the carotid branches, the superior laryngeal nerve, the recurrent laryngeal nerve, the cardiac branches, the pulmonary branches, and the abdominal branches. The superior laryngeal nerve provides sensory and motor functions, dividing into the internal laryngeal nerve supplying the larynx superior to the vocal folds, and into the external laryngeal nerve that is motor to the cricothyroid muscle of the larynx. The recurrent laryngeal nerve is sensory to the larynx inferior to the vocal folds, and motor to the intrinsic muscles of the larynx.

Regarding the special visceral efferent function, the vagus nerve innervates the voluntary muscles of the pharynx and most of the larynx, and also supplies one extrinsic muscle of the tongue. Thus, the brachial motor component of the vagus nerve provides voluntary control of the striated muscle of the pharynx, and also provides voluntary control of the striated muscle of the larynx along with the glossopharyngeal nerve (cranial nerve IX) and the trigeminal nerve (cranial nerve V). The pharyngeal nerve, the superior laryngeal nerve and the recurrent laryngeal nerve are three major branches of brachial motor fibers from the vagus nerve. The pharyngeal nerve branches from the vagus nerve just below the inferior ganglion and travels to the pharynx. The muscles innervated by the pharyngeal nerve include the superior, middle and inferior constrictor muscles, the levator palatini muscle, the salpingopharyngeus muscle, the palatopharyngeus muscle, and the palatoglossus muscle of the tongue. The superior laryngeal nerve branches from the vagus nerve just below the pharyngeal nerve and splits to form the internal and external laryngeal nerves. The external laryngeal nerve innervates the inferior constrictor muscle, and innervates the cricothyroid muscle which is involved in controlling the movements of the vocal folds. The internal laryngeal nerve pierces the thyrohyoid membrane and is a sensory nerve of the larynx. The recurrent laryngeal nerve innervates the intrinsic muscles of the larynx responsible for controlling the movement of the vocal folds.

With respect to the general visceral efferent function, the vagus nerve provides parasympathetic innervation of the smooth muscle and glands of the pharynx, larynx, and viscera of the thorax and abdomen. The parasympathetic stimulation of the vagus nerve provides a rest and digest response, that includes among other things slowing the heart rate, and stimulating increased motility.

With respect to the general visceral afferent function, the vagus nerve provides visceral sensory information from the larynx, esophagus, trachea, and abdominal and thoracic viscera, as well as the stretch receptors of the aortic arch and chemoreceptors of the aortic bodies.

With respect to the general somatic afferent function, the vagus nerve provides general sensory information from the skin of the back of the ear and external auditory meatus, parts of the external surface of the tympanic membrane, and the pharynx. The special afferent function is a minor component of the vagus nerve, providing taste sensation from the epiglottic region.

CARDIAC RHYTHM TREATMENT

Sleep apnea and hypopnea have been associated with cardiac arrhythmias and heart failure. Some embodiments of the neural stimulation therapy are integrated with or are otherwise delivered in conjunction with CRM therapies. The following section provides some information regarding pacing/defibrillation therapies, and CRT.

Pacing/Defibrillation

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses a CRM system. Such systems are often implanted in the patient and deliver therapy to the heart.

CRM systems include, among other things, pacemakers. Pacemakers deliver timed sequences of low energy electrical stimuli, called pace pulses, to the heart. Intravascular leadwire or catheter (referred to as a "lead") having one or more electrodes disposed in or about the heart can be used to deliver the stimulation. Some embodiments use a "planet" IMD wirelessly connected to "satellite" electrodes to deliver the stimulation. Heart contractions are initiated in response to such pace pulses. By properly timing the delivery of pace pulses, the heart can be induced to contract in proper rhythm, greatly improving its efficiency as a pump. Pacemakers are often used to treat patients with bradyarrhythmias, that is, hearts that beat too slowly, or irregularly.

A variety of cardiac pacemakers are known and commercially available. Pacemakers are generally characterized by a number of different aspects of their construction or use, such as which chambers of the heart they are capable of sensing, the chambers to which they deliver pacing stimuli, and their responses, if any, to sensed intrinsic electrical cardiac activity. Some pacemakers deliver pacing stimuli at fixed, regular intervals without regard to naturally occurring cardiac activity. Some pacemakers sense electrical cardiac activity in one or more of the chambers of the heart, and inhibit or trigger delivery of pacing stimuli to the heart based on the occurrence and recognition of sensed intrinsic electrical events. One such pacemaker, for example, senses electrical cardiac activity in the ventricle of the patient's heart, and delivers pacing stimuli to the ventricle only in the absence of electrical signals indicative of natural ventricular contractions. Another type of pacemaker, on the other hand, senses electrical signals in both the atrium and ventricle of the patient's heart, and delivers atrial pacing stimuli in the absence of signals indicative of natural atrial contractions, and ventricular pacing stimuli in the absence of signals indicative of natural ventricular contractions. The delivery of each pacing stimulus by the second type of pacemaker is timed using prior sensed or paced events.

Pacemakers are also known which respond to other types of physiologically-based signals, such as signals from sensors for measuring the pressure inside the patient's ventricle or for measuring the level of the patient's physical activity. In some rate-responsive pacemakers, the pacing rate is determined according to the output from an activity sensor. The pacing rate is variable between a predetermined maximum and minimum level, which may be selectable from among a plurality of programmable upper and lower rate limit settings. When the activity sensor output indicates that the patient's activity level has increased, the pacing rate is increased from the programmed lower rate by an incremental amount which is determined as a function of the output of the activity sensor.

CRM systems also include defibrillators that are capable of delivering higher energy electrical stimuli to the heart. Such defibrillators also include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart is not allowed sufficient time to fill with blood before contracting to expel the blood. Such pumping by the heart is inefficient. A defibrillator is capable of delivering an high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. Some CRM systems also are pacemakers/defibrillators that combine the functions of pacemakers and defibrillators, drug delivery devices, and any other implantable or external systems or devices for diagnosing or treating cardiac arrhythmias.

Cardiac Resynchronization Therapy (CRT)

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation.

As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) accounts for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed CRT. Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

Clinical data has shown that CRT, achieved through synchronized biventricular pacing, results in a significant improvement in cardiac function. It has also been reported CRT can be beneficial in preventing and/or reversing the ventricular remodeling that often occurs in post-MI and heart failure patients. An embodiment of the present subject matter relates to an implantable cardiac device capable of providing remodeling control therapy (RCT) by controlling ventricular activation with cardiac resynchronization pacing of the myocardium.

As provided above, neural stimulation is applied to the vagus nerve with appropriate parameters to provide therapy for sleep disordered breathing. Neural stimulation can also be applied as part of CRT. Sympathetic inhibition, as well as parasympathetic activation, have been associated with reduced arrhythmia vulnerability following a myocardial infarction, presumably by increasing collateral perfusion of the acutely ischemic myocardium and decreasing myocardial damage. Modulation of the sympathetic and parasympathetic nervous system with neural stimulation has been shown to have positive clinical benefits, such as protecting the myocardium from further remodeling and predisposition to fatal arrhythmias following a myocardial infarction. Thus, some embodiments that provide CRT includes anti-remodeling therapy (ART) by stimulating the baroreflex in order to inhibit sympathetic activity to provide a greater therapeutic benefit than either RCT or ART individually. Additional information regarding the use of neural stimulation for anti-remodeling therapy (ART) is provided in U.S. patent application Ser. No. 10/850,341 entitled "Combined Remodeling Control Therapy and Anti-Remodeling Therapy By Implantable Cardiac Device", which is herein incorporated by reference in its entirety.

DEVICE EMBODIMENTS

Figure 1B:
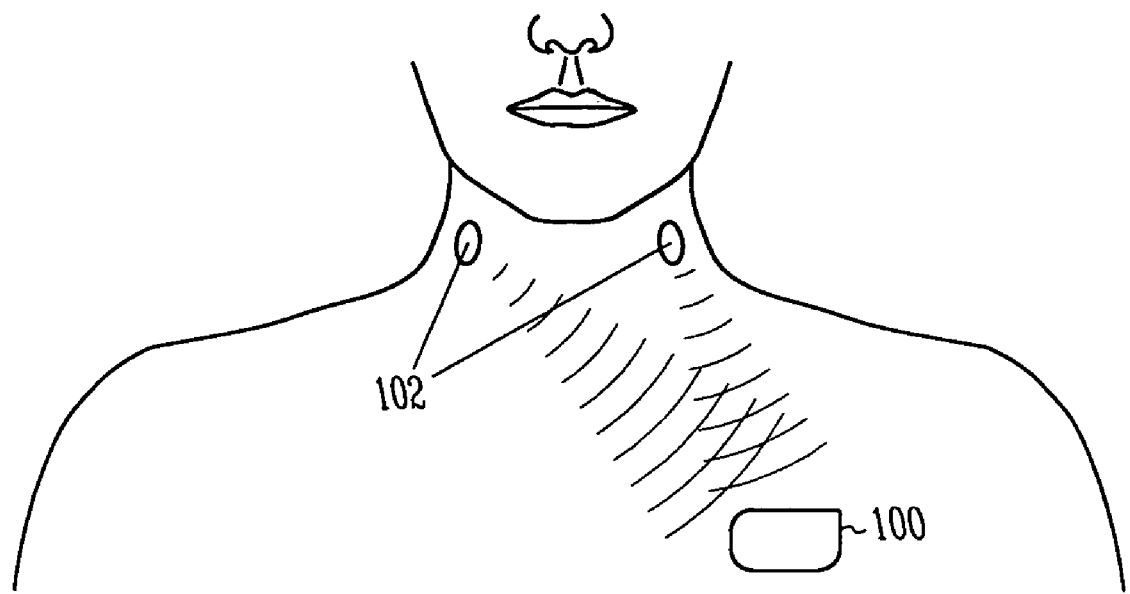

FIGS. 1A-1B illustrate some device embodiments that provide therapy for sleep disordered breathing. With reference to the illustrated embodiment in FIG. 1A, the IMD 100 includes ports for connecting lead(s) 101. Two leads are illustrated. Some embodiments use only one lead to stimulate neural target(s). The lead(s) 101 include electrode(s) adapted to provide the appropriate stimulation vectors for the neural target(s). Examples of neural targets include the superior laryngeal nerve, the recurrent laryngeal nerve and the vagus nerve. The IMD 100 includes circuitry to control the generation and delivery of the electrical stimulation to the electrode(s) on the lead(s). Some embodiments use subcutaneously-fed leads to position the electrode(s) proximate to the neural target, using a nerve cuff electrode, for example. Some embodiments use intravascularly-fed leads to position electrode(s) within a vessel adjacent to a neural target to transvascularly stimulate the neural target(s). FIG. 1B illustrates a neural stimulation embodiment in a planet-satellite configuration. The IMD 100 functions as a planet, and the electrode(s) 102 function as satellites wirelessly linked to the planet. Power and data can be sent over the wireless link using, for example, radio frequency or ultrasound technology. Examples of satellite electrodes include subcutaneous electrodes, nerve cuff electrodes and intravascular electrodes.

Figure 2A:
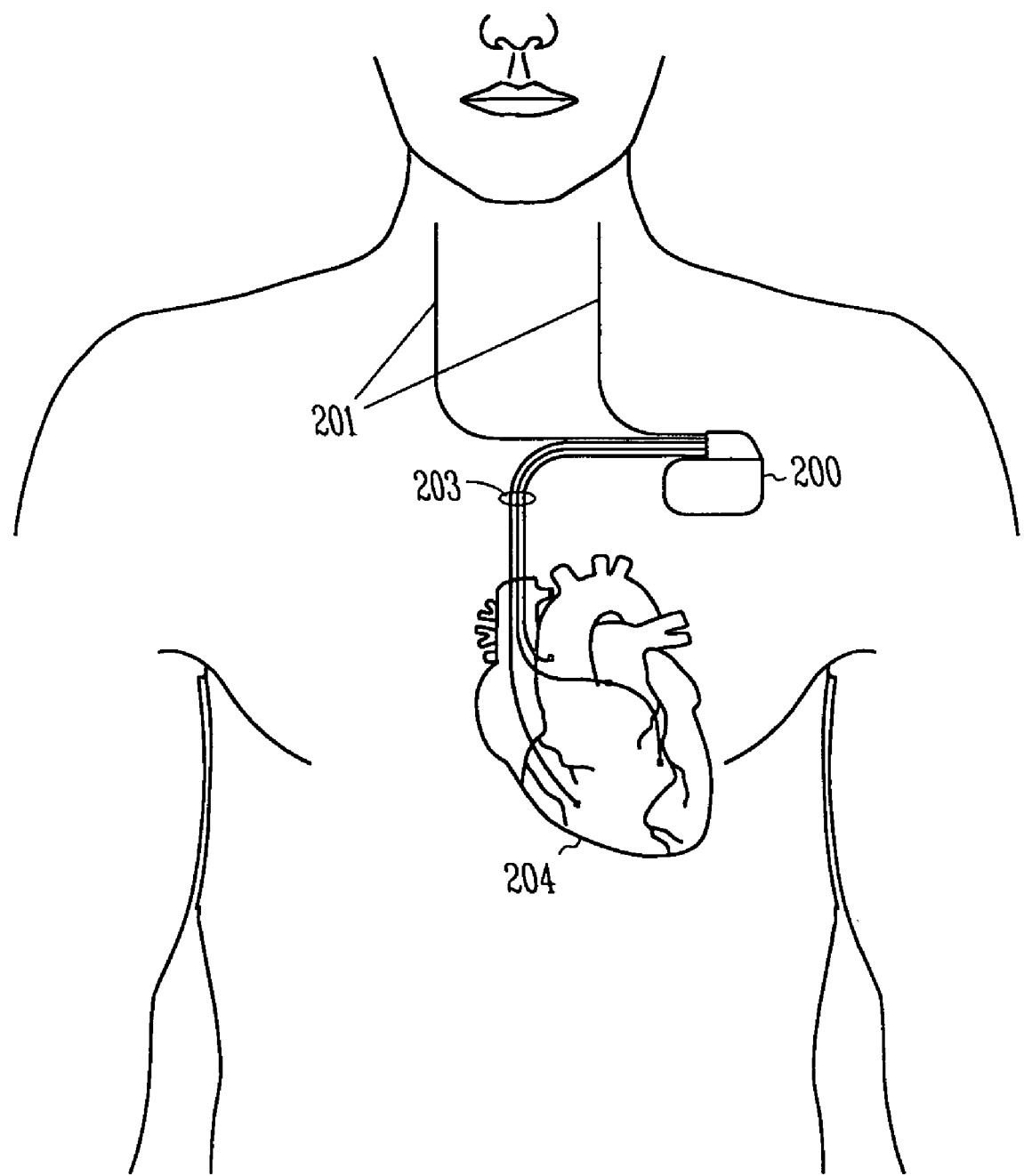
FIGS. 2A-2B illustrate some device embodiments that provide therapy for sleep disordered breathing and CRM therapy.
Figure 2B:
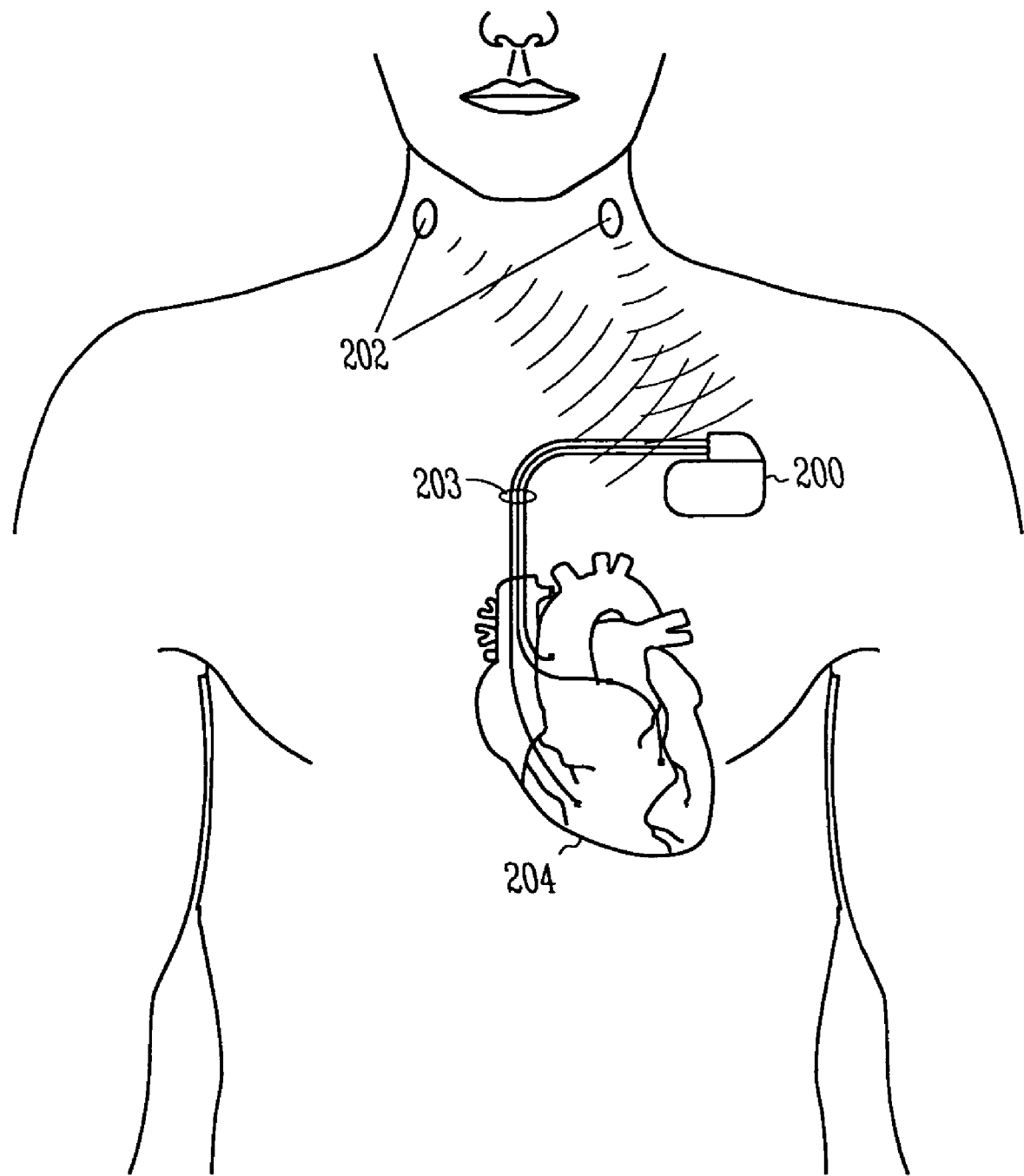

FIGS. 2A-2B illustrate some device embodiments that provide therapy for sleep disordered breathing and CRM therapy. FIG. 2A illustrates an IMD 200 placed subcutaneously or submuscularly in a patient's chest with lead(s) 203 positioned to provide a CRM therapy to a heart 204, and with lead(s) 201 positioned to stimulate at least one superior laryngeal nerve, inferior (recurrent) laryngeal nerve and vagus nerve as part of a therapy for sleep disordered breathing. According to various embodiments, the leads 203 are positioned in or proximate to the heart to provide a desired cardiac pacing therapy. In some embodiments, the lead(s) 203 are positioned in or proximate to the heart to provide a desired defibrillation therapy. In some embodiments, the lead(s) 203 are positioned in or proximate to the heart to provide a desired CRT therapy. Some embodiments place the leads in positions with respect to the heart that enable the lead(s) to deliver the combinations of at least two of the pacing, defibrillation and CRT therapies. According to various embodiments, neural stimulation lead(s) 201 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein.

FIG. 2B illustrates an implantable medical device (IMD) 200 with lead(s) 203 positioned to provide a CRM therapy to a heart 204, and with satellite electrode(s) 202 positioned to stimulate at least one neural target as part of a therapy for sleep disordered breathing. The satellite electrode(s) are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite electrodes include subcutaneous electrodes, nerve cuff electrodes and intravascular electrodes.

Figure 3:
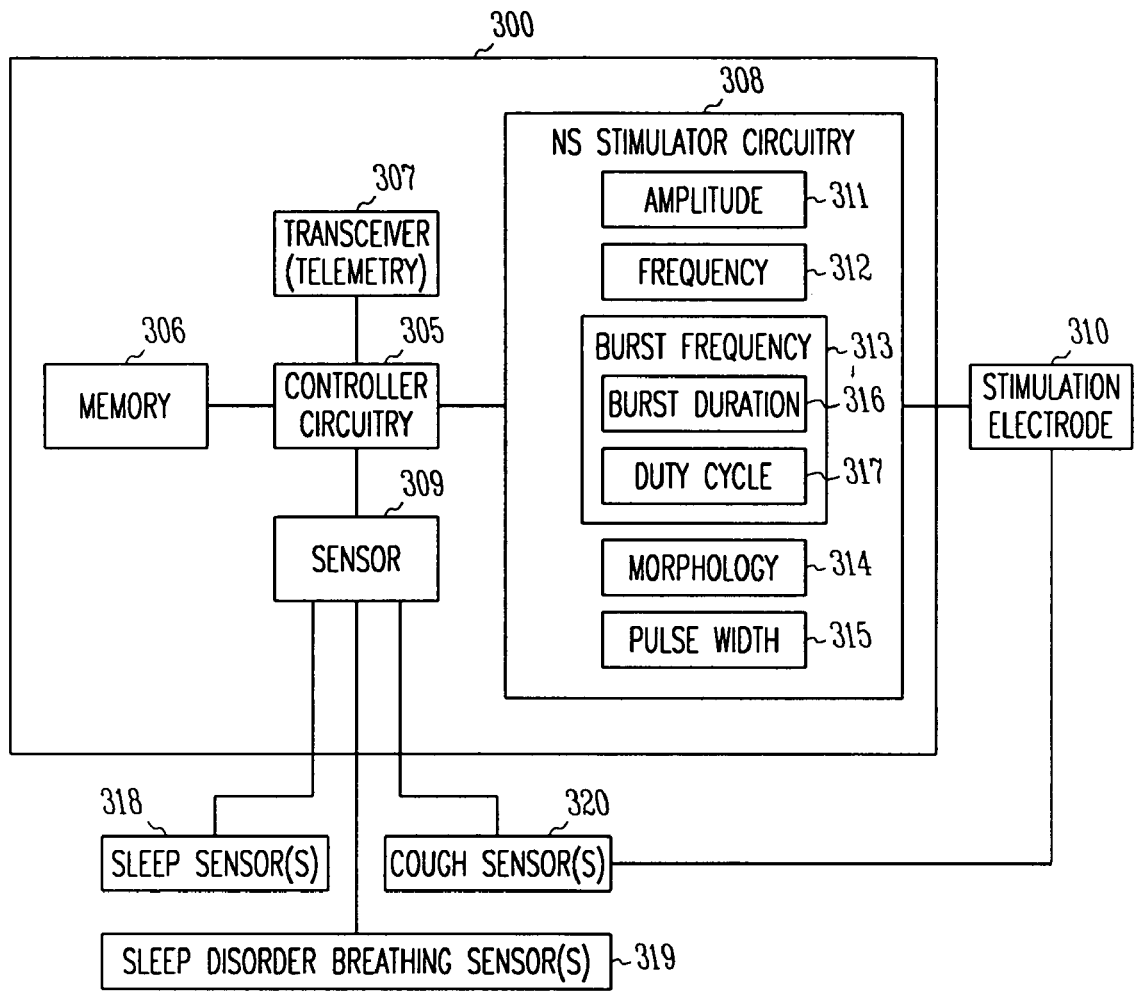
FIG. 3 illustrates an implantable medical device (IMD), according to various embodiments of the present subject matter.

FIG. 3 illustrates an implantable medical device (IMD) 300, according to various embodiments of the present subject matter. The illustrated IMD 300 provides neural stimulation signals for delivery to predetermined neural targets to treat sleep disordered breathing. The illustrated device 300 includes controller circuitry 305 and memory 306. The controller circuitry 305 is capable of being implemented using hardware, software, and combinations of hardware and software. For example, according to various embodiments, the controller circuitry 305 includes a processor to perform instructions embedded in the memory 306 to perform functions associated with the neural stimulation therapy. For example, the illustrated device 300 further includes a transceiver 307 and associated circuitry for use to communicate with a programmer or another external or internal device. Various embodiments have wireless communication capabilities. For example, some transceiver embodiments use a telemetry coil to wirelessly communicate with a programmer or another external or internal device.

The illustrated device 300 further includes neural stimulation circuitry 308. Various embodiments of the device 300 also includes sensor circuitry 309. According to some embodiments, one or more leads are able to be connected to the sensor circuitry 309 and neural stimulation circuitry 308. Some embodiments use wireless connections between the sensor(s) and sensor circuitry, and some embodiments use wireless connections between the stimulator circuitry and electrodes. The neural stimulation circuitry 308 is used to apply electrical stimulation pulses to desired neural targets, such as through one or more stimulation electrodes 310 positioned at predetermined location(s). The sensor circuitry is used to detect and process autonomic nervous system (ANS) nerve activity. In various embodiments, the sensor circuitry is further used to detect and process surrogate parameters such as blood pressure, respiration and the like, to determine the ANS activity.

According to various embodiments, the stimulation circuitry 308 includes modules to set or adjust any one or any combination of two or more of the following pulse features: the amplitude 311 of the stimulation pulse, the frequency 312 of the stimulation pulse, the burst frequency 313 of the pulse, the wave morphology 314 of the pulse, and the pulse width 315. The illustrated burst frequency 313 pulse feature includes burst duration 316 and duty cycle 317, which can be adjusted as part of a burst frequency pulse feature or can be adjusted separately. For example, a burst frequency can refer to the number of bursts per minute. Each of these bursts has a burst duration (an amount of time bursts of stimulation are provided) and a duty cycle (a ratio of time where stimulation is provided to total time). Thus, by way of example and not limitation, six bursts can be delivered during a one minute stimulation time (burst duration), where the length (pulse width) of each burst is five seconds and the time period between bursts is five seconds. In this example, the burst frequency is six burst per minute, the burst duration is 60 seconds, and the duty cycle is 50% ((6 bursts×5 sec./burst)/60 seconds). Additionally, the duration of one or more bursts can be adjusted without reference to any steady burst frequency. For example, a single stimulation burst of a predetermined burst duration or a pattern of bursts of predetermined pulse width(s) and burst timing can be provided in response to a sensed signal. Furthermore, the duty cycle can be adjusted by adjusting the number of bursts and/or adjusting the duration of one or more bursts, without requiring the bursts to be delivered with a steady burst frequency. Examples of wave morphology include a square wave, triangle wave, sinusoidal wave, and waves with desired harmonic components to mimic white noise such as is indicative of naturally-occurring baroreflex stimulation. Additionally, various controller embodiments are capable of controlling a duration of the stimulation.

The illustrated sensors connected to the sensor circuitry 309 includes sleep sensor(s) 318, sleep disordered breathing sensor(s) 319, and cough sensor(s) 320. According to various embodiments, a sleep input such as a clock or the illustrated sleep sensor(s) are used to detect sleep, and initiate a process to detect an apneic event; the sleep disordered breathing sensor(s) are used to detect sleep apnea and initiate the neural stimulation therapy at an autonomic neural target to induce a cough and terminate the sleep apnea, or can be used to detect the termination of the apneic event; and the cough sensor(s) are used to detect the physiological effect of the neural stimulation therapy (as illustrated by the dotted line) for use as feedback for the neural stimulation therapy. Examples of sleep sensors or inputs to identify sleep events include: activity sensors (e.g. accelerometer), body position/posture (e.g. three dimensional accelerometer), body temperature, muscle tone (e.g. EMG), ECG (e.g. heart rate, AV conduction time, QT interval), respiration sensors (e.g. respiratory rate, tidal volume, minute ventilation), location sensors to detect position near bed, for example, light sensors, and time of day (e.g. historical sleep times). Electroencephalograms (EEG), electrooculograms (EOG), and electromyograms (EMG) can also be used to identify sleep events. Examples of sleep disordered breathing sensors include sensors to detect body movement, heart rate, QT interval, eye movement, respiration rate, transthoracic impedance, tidal volume, minute ventilation, body posture, muscle tone, body temperature and pulse oximetry. Sleep disordered breathing can also be detected by electroencephalogram (EEG), electroneurogram (ENG), electrocardiogram (ECG), electrooculogram (EOG), electromyogram (EMG). The time of day can also be used to determine sleep disordered breathing. Sleep apnea can also be sensed using intra-cardiac pressure sensors, and activity, arousal snore sensors (e.g. accelerometer based). Examples of cough sensors include: acoustic sensors (e.g. accelerometer based), motion or vibration sensors (e.g. accelerometer based), thoracic pressure sensors, trans-thoracic impedance sensor, respiratory effort sensors, flow sensors, and EMG (e.g. diaphragm). Various combinations of these sensors can be used together.

Figure 4:
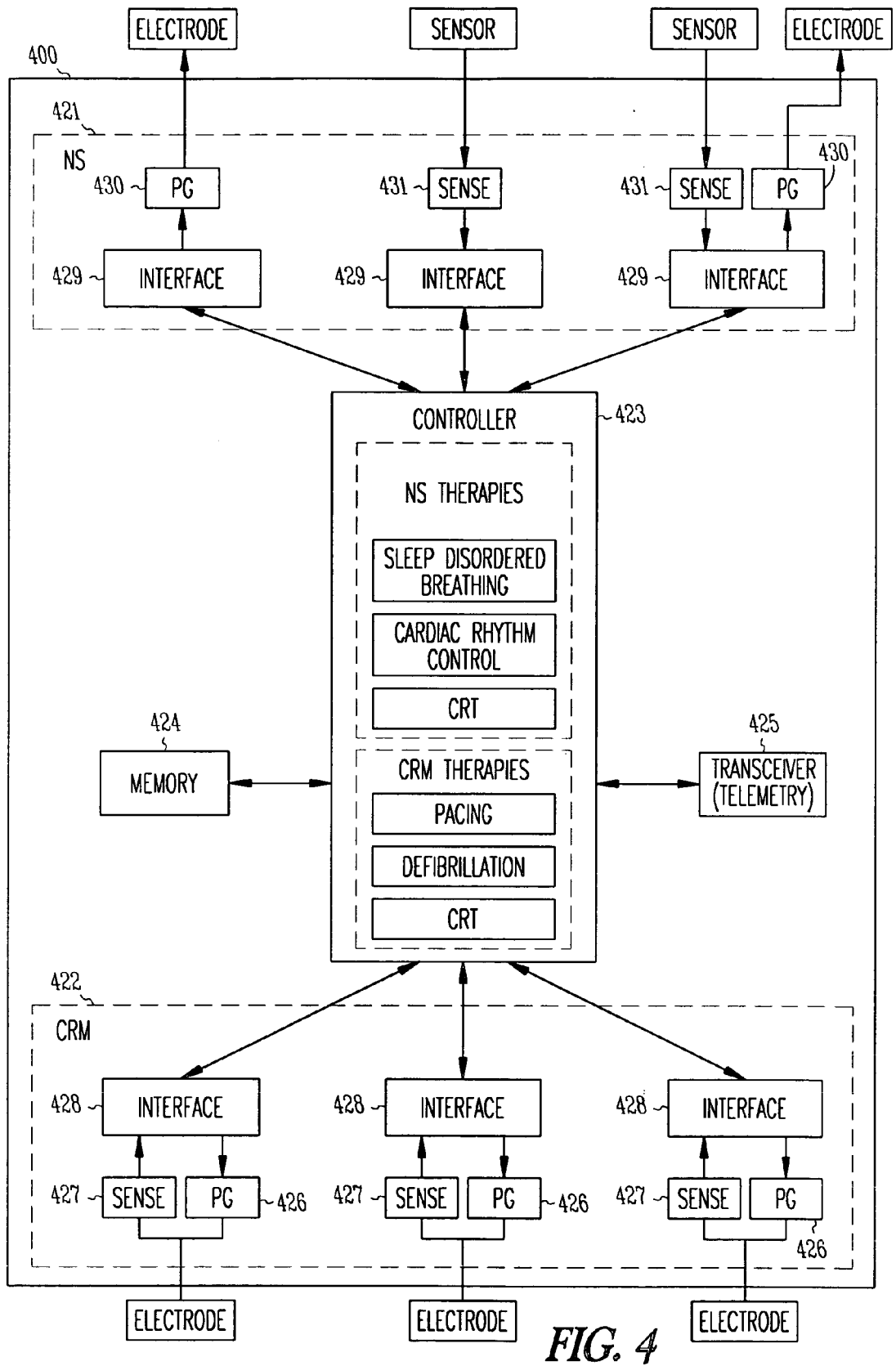
FIG. 4 illustrates an implantable medical device (IMD) having a neural stimulation (NS) component and cardiac rhythm management (CRM) component, according to various embodiments of the present subject matter.

FIG. 4 illustrates an implantable medical device (IMD) 400 having a neural stimulation (NS) component 421 and CRM component 422, according to various embodiments of the present subject matter. The illustrated device includes a controller 423 and memory 424. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. According to various embodiments, the controller includes a processor to execute instructions embedded in memory to perform the neural stimulation and CRM functions. As illustrated, the controller is adapted to provide neural stimulation to provide therapy for sleep disordered breathing, for CRM by stimulating appropriate nerves to adjust the rate and/or conduction for the heart, and CRT (ART). The illustrated controller also is adapted to provide myocardial stimulation to provide pacing, defibrillation and CRT (RCT). The illustrated device further includes a transceiver 425 and associated circuitry for use to communicate with a programmer or another external or internal device. Various embodiments include a telemetry coil.

The CRM therapy section 422 includes components, under the control of the controller, to stimulate a heart and/or sense cardiac signals using one or more electrodes. The CRM therapy section includes a pulse generator 426 for use to provide an electrical signal through an electrode to stimulate a heart, and further includes sense circuitry 427 to detect and process sensed cardiac signals. An interface 428 is generally illustrated for use to communicate between the controller 423 and the pulse generator 426 and sense circuitry 427. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 421 includes components, under the control of the controller, to stimulate a neural stimulation target and/or sense parameters associated with nerve activity or surrogates of nerve activity such as blood pressure and respiration. Three interfaces 429 are illustrated for use to provide ANS therapy. However, the present subject matter is not limited to a particular number interfaces, or to any particular stimulating or sensing functions. Pulse generators 430 are used to provide electrical pulses to an electrode for use to stimulate a neural stimulation target. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 431 are used to detect and process signals from a sensor, such as a sensor of nerve activity, blood pressure, respiration, and the like. The interfaces 429 are generally illustrated for use to communicate between the controller 423 and the pulse generator 430 and sense circuitry 431. Each interface, for example, may be used to control a separate lead. Various embodiments of the NS therapy section only include a pulse generator to stimulate neural targets such a vagus nerve, superior laryngeal nerve or recurrent laryngeal nerve to treat sleep disordered breathing. The pulse generator is adapted to produce and deliver the stimulation signal with appropriate parameters effective to induce a cough and terminate apneic events.

Figure 5:
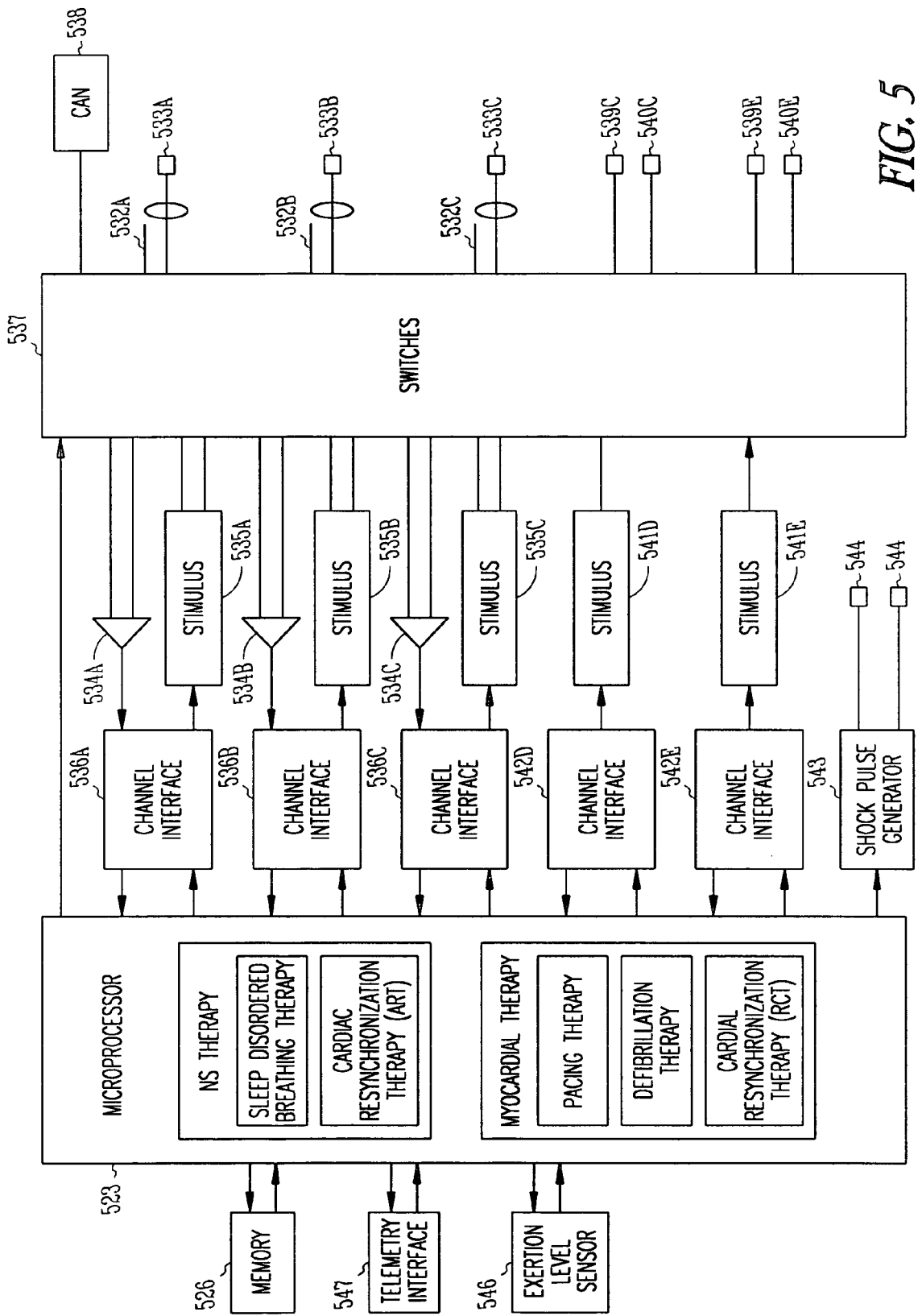
FIG. 5 shows a system diagram of an embodiment of a microprocessor-based implantable device.

FIG. 5 shows a system diagram of an embodiment of a microprocessor-based implantable device. The device is equipped with multiple sensing and pacing channels which may be physically configured to sense and/or pace multiple sites in the atria or the ventricles, and to provide neural stimulation. The illustrated device can be configured for myocardial stimulation (pacing, defibrillation, CRT/RCT) and neural stimulation (therapy of sleep disordered breathing, CRM, CRT/ART). The multiple sensing/pacing channels may be configured, for example, with one atrial and two ventricular sensing/pacing channels for delivering biventricular resynchronization therapy, with the atrial sensing/pacing channel used to deliver the biventricular resynchronization therapy in an atrial tracking mode as well as to pace the atria if required. The controller 523 of the device is a microprocessor which communicates with memory 426 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor.

Shown in FIG. 5, by way of example, are three sensing and pacing channels, such as can be used to provide myocardial stimulation/pacing, designated "A" through "C" comprising bipolar leads with ring, or proximal, electrodes 532A-C and distal, or tip, electrodes 533A-C, sensing amplifiers 534A-C, pulse generators 535A-C, and channel interfaces 536A-C. Each channel thus includes a pacing channel made up of the pulse generator connected to the electrode and a sensing channel made up of the sense amplifier connected to the electrode. The channel interfaces 536A-C communicate bidirectionally with microprocessor 523, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

The electrodes of each bipolar lead are connected via conductors within the lead to a switching network 537 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring, or proximal, and tip, or distal, electrodes of a lead or in a unipolar mode using only one of the electrodes of the lead with the device housing or can 538 serving as a ground electrode.

Also shown in FIG. 5, by way of example, are nerve stimulation channels designated "D" and "E." Neural stimulation channels are incorporated into the device. These channels can be used to deliver stimulation to a vagus nerve, a superior laryngeal nerve and/or a recurrent laryngeal nerve as part of a therapy for sleep disordered breathing, and to deliver parasympathetic stimulation and/or sympathetic inhibition for cardiac rhythm management and/or for ART as part of CRT. The illustrated channels include leads with electrodes 539D and 540D and electrodes 539E and 540E, a pulse generator 541D and 541E, and a channel interface 542D and 542E. The illustrated bipolar arrangement is intended as a non-exclusive example. Other neural stimulation electrode arrangements are within the scope of the present subject matter. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, pulse duration, and wave morphology, for example.

A shock pulse generator 543 is also interfaced to the controller for delivering a defibrillation shock via a pair of shock electrodes 544 to the atria or ventricles upon detection of a shockable tachyarrhythmia.

The illustrated controller includes a module for controlling neural stimulation (NS) therapy and module for controlling myocardial therapy. As illustrated, the NS therapy module includes a module for controlling epilepsy therapy by controlling the vagal stimulation. Also as illustrated, the myocardial therapy module includes a module for controlling pacing therapies, and a module for controlling defibrillation therapies. The illustrated controller is also adapted to control CRT by controlling RCT (a myocardial stimulation therapy), and in some embodiments by controlling ART (a neural stimulation therapy).

The controller controls the overall operation of the device in accordance with programmed instructions stored in memory, including controlling the delivery of paces via the pacing channels, interpreting sense signals received from the sensing channels, and implementing timers for defining escape intervals and sensory refractory periods. The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. CRT is most conveniently delivered in conjunction with a bradycardia pacing mode where, for example, multiple excitatory stimulation pulses are delivered to multiple sites during a cardiac cycle in order to both pace the heart in accordance with a bradycardia mode and provide pre-excitation of selected sites. An exertion level sensor 546 (e.g., an accelerometer, a minute ventilation sensor, or other sensor that measures a parameter related to metabolic demand) enables the controller to adapt the pacing rate in accordance with changes in the patient's physical activity and can enable the controller to modulate the delivery of neural stimulation and/or cardiac pacing. A telemetry interface 547 is also provided which enables the controller to communicate with an external programmer or remote monitor.

SELECTIVE NERVE STIMULATION

Embodiments of the present subject matter stimulate selected nerve fibres in a nerve trunk. For example, the superior laryngeal nerve and recurrent laryngeal nerve are two branches of the vagus nerve, and some embodiments selectively stimulate the nerve fibres in the vagus nerve associated with the superior laryngeal nerve branch of the vagus nerve and/or the recurrent laryngeal nerve branch of the vagus nerve.

Figure 6A:
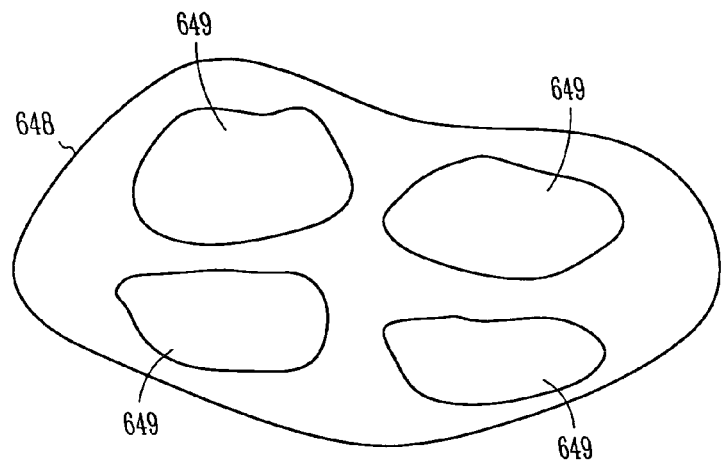
FIGS. 6A-B illustrate a nerve and a nerve cuff adapted for use in selectively stimulating the nerve, respectively, according to various embodiments.
Figure 6B:
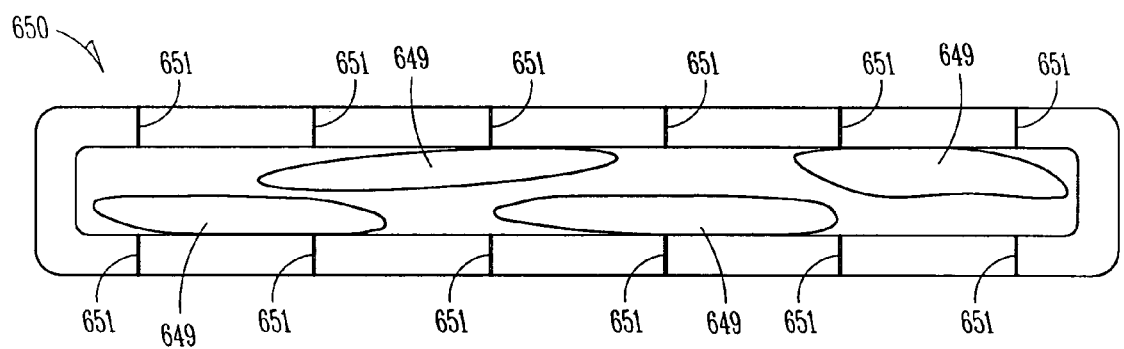

FIGS. 6A-B illustrate a nerve and a nerve cuff adapted for use in selectively stimulating the nerve, respectively, according to various embodiments. As illustrated in FIG. 6A, the nerve 648 includes a number of fasciles 649, which are groups of axons. The nerve cuff 650 illustrated in FIG. 6B has a shape adapted to flatten the nerve and spread out the fasciles 649. The nerve cuff 650 includes a number of electrodes 651. Selected electrodes can be employed to create appropriate stimulation vectors for the nerve to selectively stimulate some fasciles without stimulating other fasciles. Once the nerve cuff 650 is placed around the nerve 648, different electrode combinations can be used to create various stimulation test vectors. The physiological response is monitored for each test vector. The electrodes employed to generate the test vector associated with the desired response are used to provide the stimulation. Selective nerve stimulation using a transvascular reshaping lead has also been disclosed in U.S. patent application Ser. No. 11/130,022, entitled System For Selective Activation Of A Nerve Trunk Using A Transvascular Reshaping Lead, which is herein incorporated by reference in its entirety.

ADVANCED PATIENT MANAGEMENT

Figure 7:
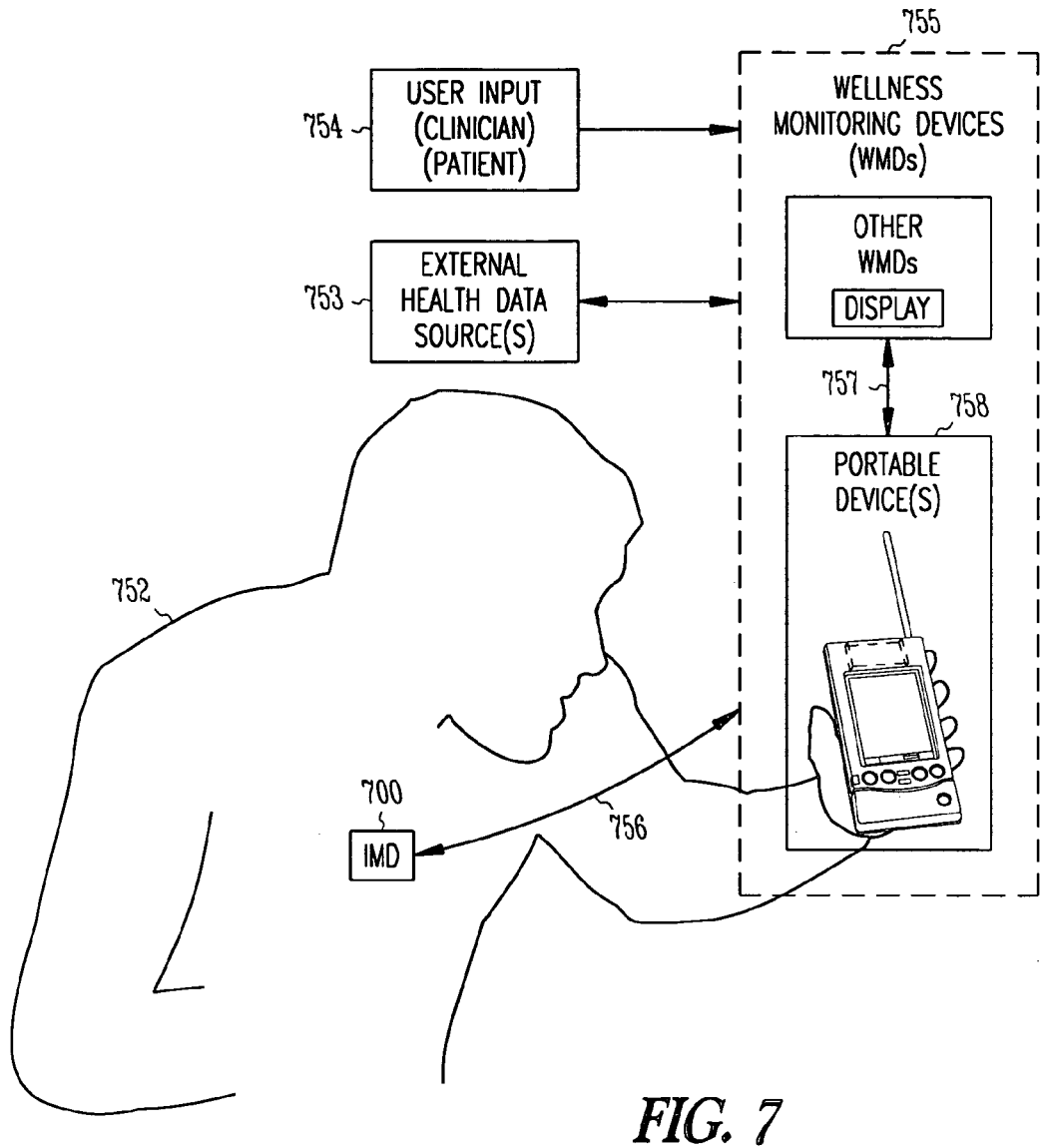
FIG. 7 illustrates an advanced patient management system according to various embodiments of the present subject matter.

Various embodiments of the present subject matter use the neural stimulation device as an IMD within an APM system. FIG. 7 illustrates an advanced patient management system according to various embodiments of the present subject matter. A patient 752 is illustrated with an implantable medical device (IMD) 700. Generally, the IMD includes one or more IMDs that provide internal therapy and/or acquire or sense internal data parameters. In various embodiments, the IMD is a neural stimulation device to treat sleep disordered breathing. In some embodiments, the IMD also functions as a CRM device that provides CRM pulsing and also senses one or more physiological parameters of a heart. Other IMDs that sense parameters and/or provide therapy, including various electrical and drug therapy, are within the scope of the present subject matter.

In various embodiments, at least one IMD 700 provides internal data such as heart rhythm, breathing, activity, and stimulation parameters, and timing. In various embodiments, IMD-provided data includes parameters sensed by the IMD and/or parameters provided by interrogating the IMD to obtain device performance status. The illustrated system also includes one or more external data source(s) 753 that provide health-related parameters. The external health-related parameters supplement the internal parameters and/or provide a diagnostic context to the internal health-related parameters. Examples of external source(s) of health data include: external sensing devices such as body temperature thermometers, blood pressure monitors, and the like; room temperature thermometers, light sensors and the like; databases such as patient history databases that are found hospitals or clinics and that may include information such as medical test results and family history; a web server database (a database accessible through a global communication network—e.g. Internet) that may include information regarding environment, medication interaction, and the like; databases and/or user inputs regarding mental/emotional and diet parameter types; and other external data sources capable of providing health-related parameters.

The illustrated system also includes a user input 754 through which a user is able to input additional health-related parameters for use by a wellness monitoring device (WMD) 755. In various embodiments, the user input includes a touch screen on a PDA or other device, a keyboard and mouse on a computer, and the like. In various embodiments, a patient is able to input additional health-related parameters for use by the wellness monitoring device. In various embodiments, a clinician is able to input additional health-related parameters for use by the WMD.

The WMD 755 is illustrated by dotted line, and includes one or more devices. In various embodiments, the at least one IMD communicates wirelessly with at least one WMD, as shown by communication link 756. In various embodiments that include multiple WMDs, the WMDs are able to communicate with each other, as shown via communication link 757. In various embodiments, the WMD(s) includes portable devices 758 that are external to the body of patient such as a PDA, (variously referred to as a personal digital, or data, assistant), a portable telephone (including a cellular telephone or a cordless telephone), a pager (one way or two way), a handheld, palm-top, laptop, portable or notebook computer, or other such battery operated portable communication device. In various embodiments, the WMD(s) includes programmers. In various embodiments, the WMD(s) includes various non-portable devices such as larger computers or computer enterprise systems. In various embodiments of the present subject matter, the WMD (which includes one or more devices) includes a display on which parameter trends are capable of being displayed. Some WMD embodiments provide analysis of internal and external (both voluntary and involuntary) parameters. In various embodiments, the WMD includes computer and programming that conducts data analysis suitable for use in managing patient health and medical care.

Figure 8:
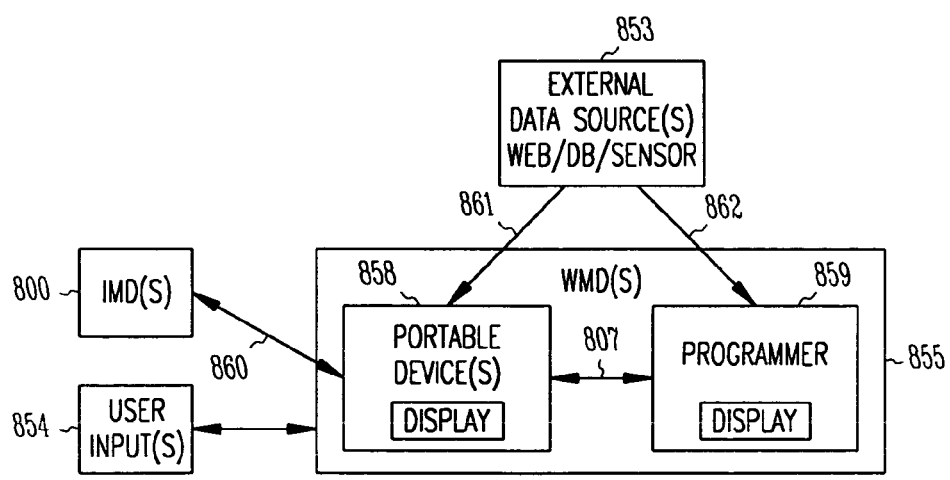
FIG. 8 illustrates an advanced patient management (APM) system according to various embodiments of the present subject matter.

FIG. 8 illustrates an APM system according to various embodiments of the present subject matter. The illustrated system includes an IMD 800 to provide neural stimulation as part of a therapy for sleep disordered breathing. In various embodiments, the IMD further includes the functions of an implantable CRM device, or other implanted medical device that provides therapy to a patient or an organ of a patient, and/or that provides data derived from measurements internal to a patient. In various embodiments, the IMD includes a device to provide drug therapy.

The illustrated system includes at least one WMD 855 that includes at least one display for displaying trended parameters. In the illustrated system, the at least one WMD includes a portable device 858 (such as a PDA) and a programmer 859. The IMD is shown coupled to the portable device by communication link 860. The portable device is further coupled to the programmer by communication link 807. Various embodiments of the present subject matter do not include the portable device. In these embodiments, the IMD is able to be coupled directly to the programmer by a communication link (not shown).

At least one external data source 853 (such as web server(s), database(s), and sensor(s)) is coupled to the WMD(s) via at least one communication link. The external data source provides external (with respect to the IMD in the patient) health-related parameters that supplement and/or provide context for the IMD parameters. In the illustrated system, a communication link 861 exists between the portable device and the external data source, and a communication link 862 exists between the programmer and the external data source. It is noted that various applications may not require both communication links 861 and 862. In the illustration, the system includes at least one user input 854 to the at least one WMD. For example, a patient is able to provide health-care information using the portable device, and a health care provider is capable of providing health-care information using the programmer.

In various embodiments, the IMD also includes circuitry and programming adapted to monitor the condition and performance of the pulse generator or other IMD. For example, in various embodiments, the IMD provides data concerning the remaining battery condition for a power supply coupled to the IMD. Such data may include information regarding remaining battery capacity or life, battery internal resistance or other measurable parameters. In various embodiments, the data includes information regarding the electrical therapy provided by the IMD. For example, in various embodiments, such data includes lead impedance, sense voltage levels, therapy history, and device therapy mode settings and parameter values.

Figure 9:
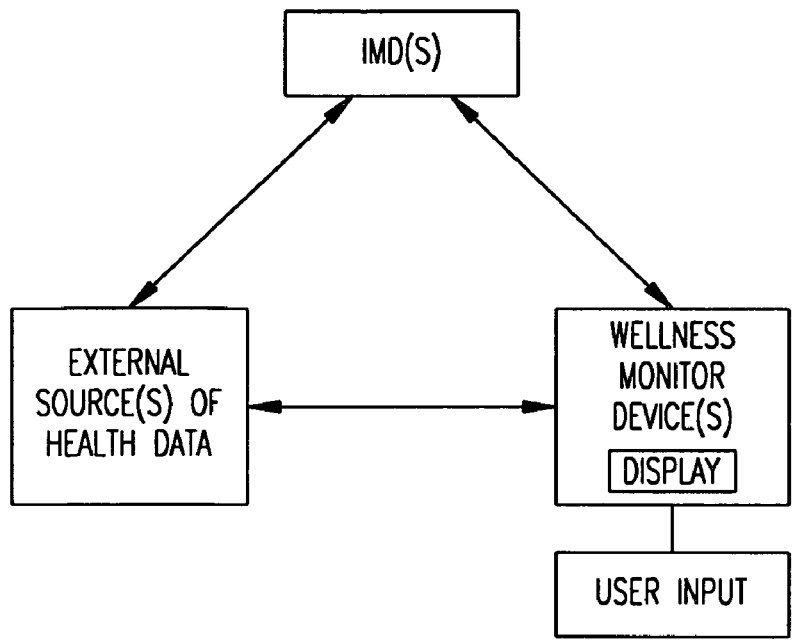
FIG. 9 illustrates an advanced patient management (APM) system having direct communication links according to various embodiments of the present subject matter.
Figure 10:
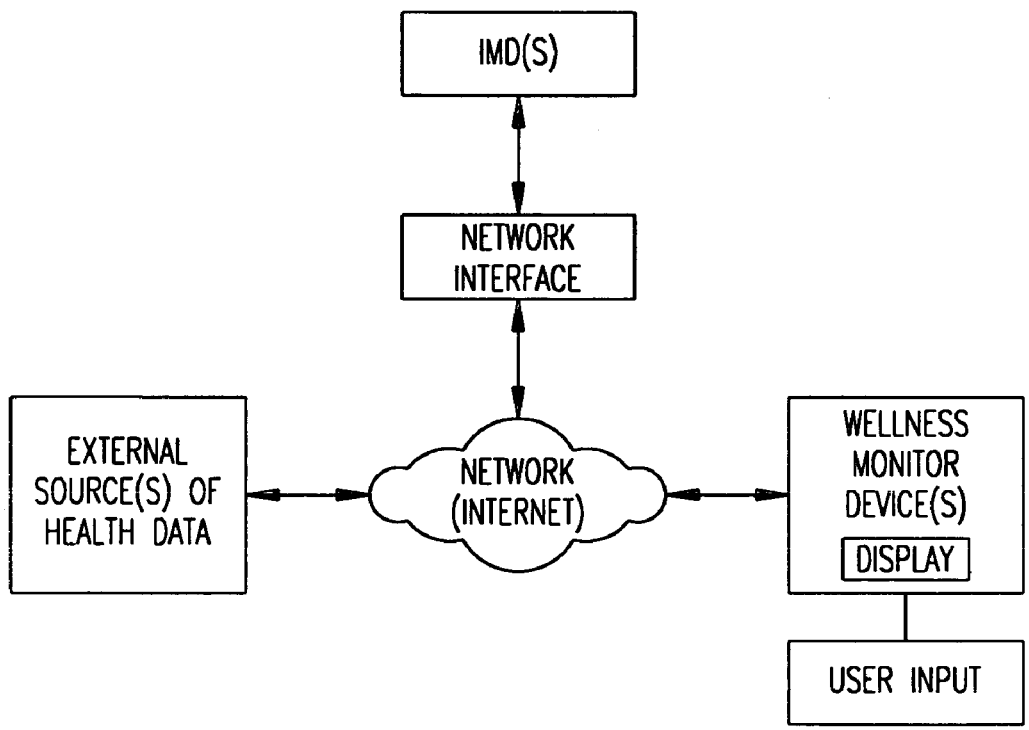
FIG. 10 illustrates an advanced patient management (APM) system having network communication links according to various embodiments of the present subject matter.

Communication between components of the APM system can be accomplished using various communication links. FIG. 9 illustrates an advanced patient management (APM) system having direct communication links according to various embodiments of the present subject matter. According to various embodiments of the system, the communication links include wired links, wireless links or both wired and wireless links. FIG. 10 illustrates an advanced patient management (APM) system having network communication links according to various embodiments of the present subject matter. According to various embodiments, the communication links include wired links, wireless links or both wired and wireless links.

THERAPY PROCESS TO TREAT SLEEP DISORDERED BREATHING

The systems and devices provided above can perform a number of processes. The following processes are provided as examples of therapies for treating sleep disordered breathing.

Figure 11:
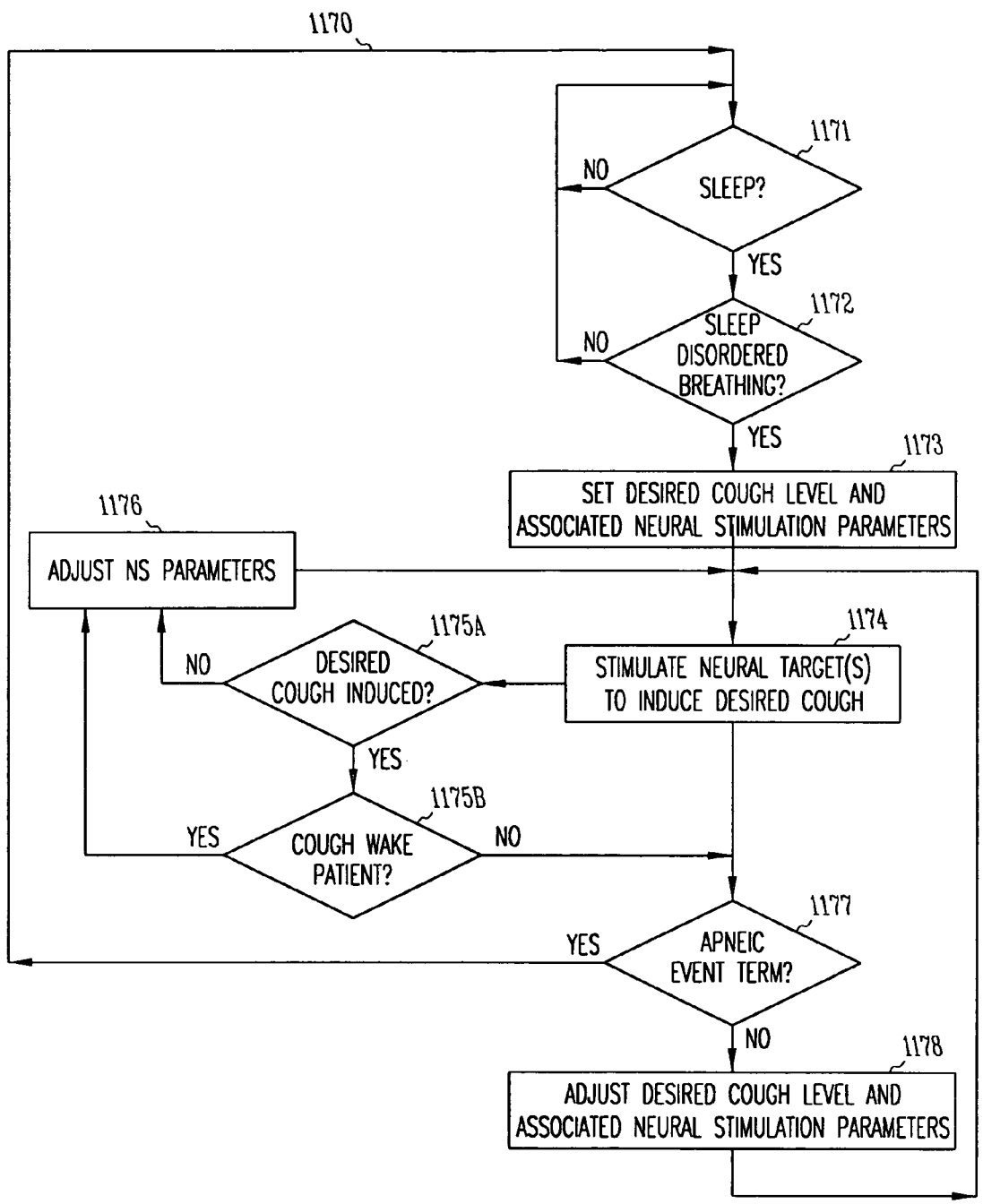
FIG. 11 illustrates a process to treat sleep disordered breathing, according to various embodiments of the present subject matter.

FIG. 11 illustrates a process to treat sleep disordered breathing, according to various embodiments of the present subject matter. Beginning at node 1170, the process identifies an occurrence of a sleep event such as determining whether the patient is sleeping at 1171. A sleep-event can also be determined using time-based and/or location-based factors, for example. If the patient is not sleeping, the process returns to node 1170. If the patient is sleeping, the process proceeds to 1172 where it is determined whether a sleep disordered breathing event is occurring. For example, a transthoracic impedance can be used to identify the presence or absence of an apneic event. If a sleep disordered breathing event is not present, then the process returns to node 1170. If a sleep disordered breathing event is present, then the process proceeds to 1173 to set the desired cough level and associated neural stimulation parameters, and to 1174 to stimulate the neural target(s) to induce a desired cough. Examples of neural targets include targets of the autonomic nervous system (ANS), including the superior laryngeal nerve, the recurrent laryngeal nerve, and the vagus nerve.

As illustrated at 1175A, some embodiments determine if the neural stimulation was effective in inducing a desired cough. If not, the neural stimulation parameters are adjusted at 1176, and the stimulation occurs at 1174 with the adjusted parameters. As illustrated at 1175B, some embodiments determine if the cough wakens the patient. For example, it may be determined that the patient is awake if the sleep sensors indicate that the patient is no longer sleeping. In another example, the present subject matter detects whether a cough causes the patient to surpass a threshold of wakefulness, which may be different then if it is determined that the patient is "not asleep." Thus, in these examples, a cough that causes some restlessness or stirring may be acceptable since the patient is able to return to a deeper sleep, even though a sleep sensor indicates that the patient is no longer asleep. If the cough wakens the patient, the neural stimulation parameters are adjusted at 1176, and stimulation occurs at 1174 with the adjusted parameters. Thus, embodiments that include 1175A, 1175B, and 1176 are useful to verify that the desired cough level has been attained by the stimulation parameters for the neural stimulation, and to appropriately adjust the stimulation parameters to achieve the desired cough level.

At 1177, it is determined whether an apneic event has been terminated. For example, transthoracic impedance can be used. If the apneic event has been terminated, the process returns to node 1170. If the apneic event has not been terminated, the process proceeds to 1178 to adjust the desired cough level and associated neural stimulation parameters intended to achieve the desired cough level, and then stimulates the neural targets, as reflected at 1174, using the adjusted neural stimulation parameters to achieve the adjusted desired cough level.

Some embodiments do not detect a cough level. For example, it can be determined whether the neural stimulation was effective in terminating the apneic event by using a sensor of the apneic event to determine if the event in fact terminated. the neural stimulation parameters can be appropriately adjusted to a level that terminates the apneic event without awakening the patient.

Figure 12:
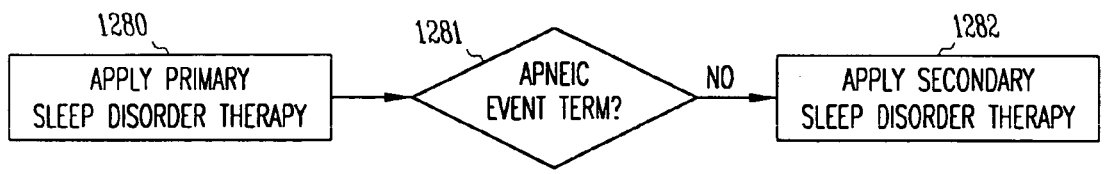
FIG. 12 illustrates an embodiment of a therapy process to treat sleep disordered breathing.

FIG. 12 illustrates an embodiment of a therapy process to treat sleep disordered breathing. At 1280, a primary sleep disorder therapy is applied. If the apneic event is not terminated, as illustrated at 1281, the process proceeds to 1282 to apply a secondary sleep disorder therapy. The neural stimulation applied to induce a cough reflex is the primary therapy in some embodiments, and is the second therapy in other embodiments. A number of other therapies can be used in conjunction with this therapy. For example, a CPAP therapy can be used, as either a primary or secondary therapy, with the present subject matter. Another therapy example includes atrial overdrive pacing, which also can be used as either a primary or secondary therapy with the present subject matter. Atrial overdrive pacing, for example, can be implemented by pacing the atria at a predetermined rate (e.g. 15 beats per minute) over the mean nocturnal rate. Atrial overdrive pacing is implemented in pacemakers to reduce the incidence of atrial tachyarrhythmias. However, studies indicate that such overdrive pacing also reduces the number of sleep apnea episodes. Thus, neural stimulator embodiments that include CRM functions are capable of inducing a cough by stimulating a neural target such as the superior laryngeal nerve, recurrent laryngeal nerve and vagus nerve, and are also capable of providing atrial overdrive pacing as a therapy for sleep disordered breathing.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined.

In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. An implantable device, comprising:
   at least one sensor for use in detecting sleep disordered breathing;
   a pulse generator adapted to deliver a first electrical signal through at least one electrode to stimulate a neural target;
   a controller adapted to communicate with the at least one sensor and with the pulse generator, the controller being adapted to detect sleep disordered breathing using the at least one sensor and provide a therapy for sleep disordered breathing in response to a detected apneic event, the therapy for sleep disordered breathing being adapted to deliver the first electrical signal through the at least one electrode to induce a cough reflex to terminate the apneic event;
   at least one cough sensor for use in detecting a cough level induced by the therapy for sleep disordered breathing,
   the controller being adapted to detect the cough level induced by the therapy for sleep disordered breathing using the at least one cough sensor, compare the detected cough level to a desired cough level, and adjust neural stimulation parameters associated with the therapy for sleep disordered breathing to induce a cough level closer to the desired cough level.

2. The device of claim 1, wherein the neural target includes the superior laryngeal nerve.

3. The device of claim 1, wherein the neural target includes the recurrent laryngeal nerve.

4. The device of claim 1, wherein the neural target includes the vagus nerve.

5. The device of claim 1, wherein the at least one electrode includes at least one nerve cuff electrode.

6. The device of claim 5, wherein the at least one nerve cuff electrode includes a selective nerve stimulation electrode adapted to selectively stimulate some nerve fibres of a nerve trunk without stimulating other nerve fibres of the nerve trunk.

7. The device of claim 1, wherein the at least one electrode includes at least one electrode adapted to be intravascularly placed to transvascularly stimulate the neural target.

8. The device of claim 7, wherein the at least one electrode adapted to be intravascularly placed includes an electrode to selectively stimulate some nerve fibres of a nerve trunk without stimulating other nerve fibres of the nerve trunk.

9. The device of claim 1, wherein the pulse generator is adapted to deliver the first electrical signal through at least one electrode via a lead connecting the pulse generator to the at least one electrode.

10. The device of claim 1, wherein the pulse generator is adapted to wirelessly deliver the first electrical signal through at least one electrode.

11. The device of claim 1, further comprising at least one sleep input for use in determining when a patient is asleep, the controller being adapted to determine when the patient is sleeping using the at least one sleep input and initiate a process to detect sleep disordered breathing when the patient is asleep.

12. The device of claim 1, further comprising at least one input for use in determining whether the therapy for sleep disordered breathing causes a patient who is receiving the therapy to awaken, the controller being adapted to adjust neural stimulation parameters associated with the therapy for sleep disordered breathing to prevent the stimulation from awakening the patient.

13. The device of claim 1, wherein the controller is configured to stop the therapy for sleep disordered breathing when the controller the sleep disordered event has been terminated.

14. The device of claim 13, wherein the at least one sensor for use in detecting sleep disordered breathing includes a transthoracic sensor.

15. The device of claim 1, wherein the implantable device is incorporated in an advanced patient management (APM) system, the APM system including a portable external device adapted to communicate with the implantable device, wherein at least one of the implantable device and the portable external device is adapted to trend data associated with the implantable medical device.

16. The device of claim 1, further comprising circuitry to sense cardiac activity and deliver a second electrical signal through at least one cardiac rhythm management (CRM) electrode based on the sensed cardiac activity to provide CRM therapy.

17. The device of claim 16, wherein the CRM therapy includes a pacing therapy.

18. The device of claim 17, wherein the pacing therapy includes atrial overdrive pacing.

19. The device of claim 17, wherein the pacing therapy includes neural stimulation delivered to a neural target to regulate heart rate.

20. The device of claim 16, wherein the CRM therapy includes a defibrillation therapy.

21. The device of claim 16, wherein the CRM therapy includes a cardiac resynchronization therapy (CRT).

22. The device of claim 21, wherein the CRT therapy includes neural stimulation delivered to a baroreflex neural target for an anti-remodeling therapy (ART).

23. A method for operating a device to terminate a sleep disordered event, wherein the device includes at least one sleep disordered breathing sensor for use in detecting a sleep disordered breathing event, a pulse generator, a controller, and at least one cough sensor, comprising:
   detecting the sleep disordered event using the at least one sleep disordered breathing sensor and the controller;
   in response to a detected sleep disordered breathing event, stimulating an autonomic neural target using the pulse generator to induce a cough through a cough reflex to terminate the sleep disordered breathing event;
   detecting a cough level using the at least one cough sensor for the cough induced by the stimulation of the autonomic neural target;
   using the controller to compare the detected cough level to a desired cough level; and
   adjusting stimulation parameters for the autonomic neural target, using the controller, to induce a cough with a cough level closer to the desired cough level.

24. The method of claim 23, wherein
   stimulating the autonomic target includes stimulating a superior laryngeal nerve, a recurrent laryngeal nerve or a vagus nerve.

25. The method of claim 24, further comprising determining that the sleep disordered breathing event terminated, and stopping stimulation of the neural target in response to the terminated sleep disordered breathing event.

26. The method of claim 24, further comprising:
   identifying a sleep event; and
   in response to identifying the sleep event, initiating a process to detect the sleep disordered breathing event.

27. The method of claim 24, further comprising:
    determining patient wakefulness; and
    adjusting stimulation parameters to prevent awakening the patient.

28. The method of claim 24, wherein the neural target includes the superior laryngeal nerve.

29. The method of claim 24, wherein the neural target includes the recurrent laryngeal nerve.

30. The method of claim 24, wherein the neural target includes the vagus nerve.

31. The method of claim 24, wherein stimulating the autonomic neural target includes selectively stimulating nerve fibres of a nerve trunk without stimulating other nerve fibres of the nerve trunk.

32. The method of claim 24, wherein the method is a primary method used in conjunction with another method to treat sleep disorders.

33. The method of claim 24, wherein the method is a secondary method used in conjunction with another method to treat sleep disorders.

* * * * *

UNITED STATES PATENT AND TRADEMARK OFFICE
CERTIFICATE OF CORRECTION

| | | |
|---|---|---|
| PATENT NO. | : 7,672,728 B2 | Page 1 of 1 |
| APPLICATION NO. | : 11/320500 | |
| DATED | : March 2, 2010 | |
| INVENTOR(S) | : Imad Libbus et al. | |

It is certified that error appears in the above-identified patent and that said Letters Patent is hereby corrected as shown below:

In column 20, line 6, in Claim 13, delete "when the controller the sleep disordered even" and insert -- when the controller determines that the sleep disordered event --, therefor.

In column 20, line 42, in Claim 23, delete "event" and insert -- breathing event --, therefor.

Signed and Sealed this

Eighteenth Day of May, 2010

David J. Kappos
*Director of the United States Patent and Trademark Office*